United States Patent
Almulhim

(10) Patent No.: US 11,759,367 B1
(45) Date of Patent: Sep. 19, 2023

(54) CORRECTION AND PROTECTION TOOL FOR INGROWN TOENAIL

(71) Applicant: KING FAISAL UNIVERSITY, Al-Ahsa (SA)

(72) Inventor: Abdulrahnman Saleh Almulhim, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/116,450

(22) Filed: Mar. 2, 2023

(51) Int. Cl.
A61F 13/06 (2006.01)
A61F 13/00 (2006.01)

(52) U.S. Cl.
CPC ........... *A61F 13/00025* (2013.01); *A61F 2013/00119* (2013.01); *A61F 2013/00353* (2013.01)

(58) Field of Classification Search
CPC ...... A61F 13/00025; A61F 2013/00119; A61F 2013/00353; A61F 13/063; A61F 13/064; A44C 15/008; A45D 29/004
USPC ........................................ 132/285
See application file for complete search history.

(56) References Cited

U.S. PATENT DOCUMENTS

| | | | |
|---|---|---|---|
| 2,283,703 A * | 5/1942 | Stedman | A45D 29/004 132/285 |
| 3,132,648 A | 5/1964 | Scholl | |
| 3,476,109 A * | 11/1969 | Hurney | A61F 13/105 128/892 |
| 4,858,245 A | 8/1989 | Sullivan et al. | |
| 6,139,514 A | 10/2000 | Benson | |
| 7,249,385 B2 | 7/2007 | Schukraft | |
| D799,710 S * | 10/2017 | Wong | D24/190 |
| 10,231,527 B2 * | 3/2019 | Davis | A45D 29/00 |
| 11,266,538 B2 | 3/2022 | Francis | |
| 2010/0100025 A1 | 4/2010 | Kane | |

* cited by examiner

*Primary Examiner* — Camtu T Nguyen
(74) *Attorney, Agent, or Firm* — Nath, Goldberg & Meyer; Richard C. Litman

(57) ABSTRACT

A correction protection tool for an ingrown toenail includes an armor stocking having a first armor stocking end and a second armor stocking end. The first armor stocking end has a first armor stocking end opening to receive a toe. The second armor stocking end has a second armor stocking end opening to expose a toenail of the toe. An armor cone has a first armor cone end and a second armor cone end. The first armor cone end has a first armor cone end opening to receive the armor stocking. The second armor cone end surrounds the second armor stocking end to protect the toenail.

9 Claims, 1 Drawing Sheet

CORRECTION AND PROTECTION TOOL FOR INGROWN TOENAIL

BACKGROUND

1. Field

The present disclosure relates to the correction and protection of an ingrown toenail, and more particularly to a tool and method of correction and protection for an ingrown toenail.

2. Description of the Related Art

Treatment of an ingrown toenail has focused on treating the damaged area of a toe. A bandage like treatment is used which absorbs any secretions. This may be a soft tight fitting bandage which also includes medications to assist in healing the damaged area and prevent infections. An outer cover has also been contemplated which assists in protecting the damaged area. Some problems with this type of treatment is that the bandage does not assist in preventing the toenail from again becoming ingrown and the bandage may not allow enough air into the damaged area for proper recovery. The damaged area is also covered by the bandage which makes it hard to examine the damaged area without removing the bandage.

Thus, new ingrown toenail treatments solving the aforementioned problems are desired.

SUMMARY

The correction and protection of an ingrown toenail as disclosed herein overcomes the problems of the related art.

A correction protection tool for an ingrown toenail, in one embodiment, includes an armor stocking having a first armor stocking end and a second armor stocking end. The first armor stocking end has a first armor stocking end opening to receive a toe. The second armor stocking end has a second armor stocking end opening to expose a toenail of the toe. The tool can further comprise an armor cone having a first armor cone end and a second armor cone end. The first armor cone end has a first armor cone end opening to receive the armor stocking. The second armor cone end surrounds the second armor stocking end to protect the toenail.

The second armor stocking end opening fits around the toenail to elevate an edge of the toenail to assist in correcting the toenail from being ingrown.

In one embodiment, the first armor stocking end can further include an armor stocking self-adhesive bandage to fix to the armor stocking to the base of the toe.

In an embodiment, the armor stocking is made of an elastic, soft, flexible silicone that fits around the toe.

In another embodiment, the first armor cone end can include an armor cone self-adhesive bandage.

In a further embodiment, the second armor cone end includes a second armor cone end opening at a tip of the second armor cone end allowing for inspection of the toenail.

In yet another embodiment, the armor cone is a hard silicone cover that protects the toe.

A correction protection tool for an ingrown toenail, in another embodiment, includes an armor stocking having a first armor stocking end and a second armor stocking end. The first armor stocking end has a first armor stocking end opening to receive a toe and an armor stocking self-adhesive bandage to adhere the armor stocking to a base of the toe. The second armor stocking end has a second armor stocking end opening to expose a toenail of the toe. The second armor stocking end opening fits around the toenail to elevate an edge of the toenail to assist in correcting the toenail from being ingrown. The tool can further comprsie an armor cone having a first armor cone end and a second armor cone end. The first armor cone end has a first armor cone end opening to receive the armor stocking and an armor cone self-adhesive bandage. The second armor cone end surrounds the second armor stocking end to protect the toenail and has an opening at a tip of the second armor cone end allowing for inspection of the toenail.

In an embodiment, the armor stocking is made of an elastic, soft, flexible silicone that fits around the toe.

In another embodiment, the armor cone is a hard silicone cover that protects the toe.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
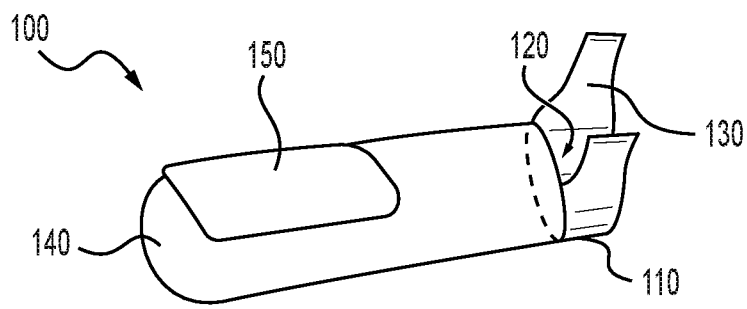
FIG. 1 is an illustration of an armor stocking.

FIG. 1 is an illustration of an armor stocking 100. A first armor stocking end 110 has a first armor stocking end opening 120 and an armor stocking self-adhesive bandage 130. The first armor stocking end opening 120 can receive a toe of a patient, after which the armor stocking self-adhesive bandage 130 can be applied to the base of the toe.

A second armor stocking end 140 includes a second armor stocking end opening 150 that fits around a toenail of the toe to elevate an edge of the toenail to assist in correcting the toenail from being ingrown.

The armor stocking 100 is, in some embodiments, made of an elastic, soft, flexible silicone that fits around the toe.

Figure 2:
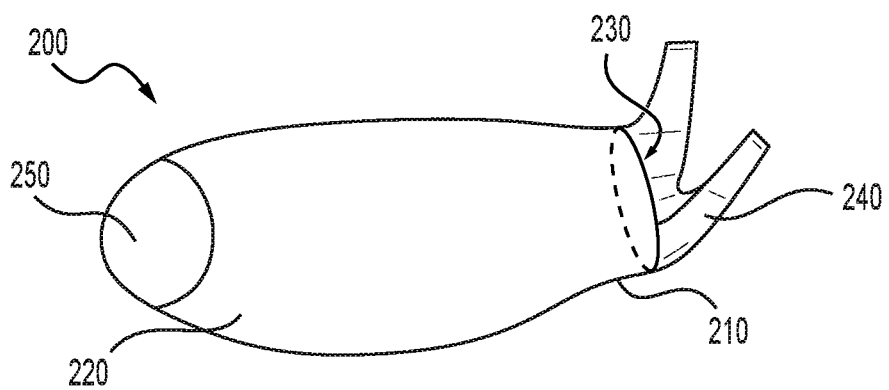
FIG. 2 is an illustration of an armor cone.

FIG. 2 is an illustration of an armor cone 200 having a first armor cone end 210 and a second armor cone end 220. The first armor cone end 210 has a first armor cone end opening 230 to receive the armor stocking 100. The second armor cone end 220 surrounds the second armor stocking end 140 to protect the toenail.

The first armor cone end 210 can include an armor cone self-adhesive bandage 240.

A second armor cone end opening 250 can be located at a tip of the second armor cone end 220 allowing for inspection of the toenail.

The armor cone 200 is, in some embodiments, a hard silicone cover that protects the toe.

Figure 3:
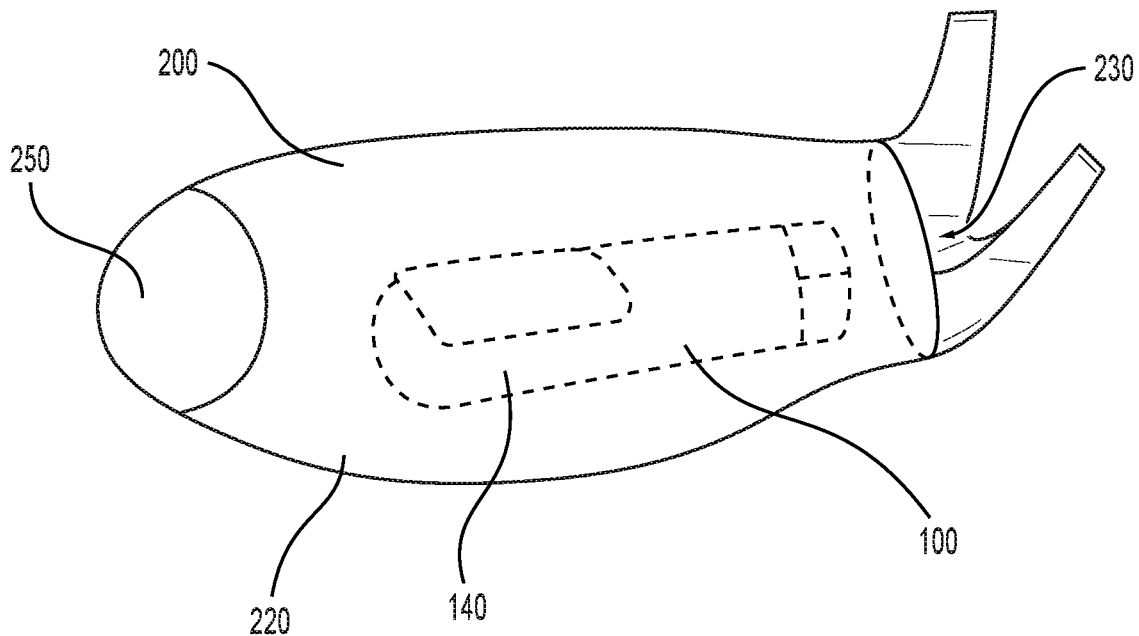
FIG. 3 is an illustration of the armor stocking fitted within the armor cone.

FIG. 3 is an illustration of the armor stocking 100 fitted within the armor cone 200. Once a toe is placed within the armor stocking 100, the armor stocking 100 can be placed within the armor cone 200 through the first armor cone end opening 230. The second armor cone end 220 serves to cover and protect the second armor stocking end 140. The second armor cone end opening 250 allows for inspection of the toenail.

A patient with an ingrown toenail often seeks medical treatment to alleviate pain and discomfort. A medical professional can treat the affected toe and then must ensure proper recovery. The armor stocking 100 can be used for proper recovery by inserting the toe into the armor stocking 100 through the first armor stocking end opening 120. This will expose the toenail through the second armor stocking end opening 150 which fits around a toenail of the toe to elevate an edge of the toenail to assist in correcting the toenail from being ingrown. The armor stocking self-adhesive bandage 130 is then applied to the base of the toe.

Protection of the toenail is accomplished by inserting the toe with the armor stocking 100 into the armor cone 200 through the first armor cone end opening 230. The armor cone 200 is a hard silicone cover that protects the toe. The armor cone self-adhesive bandage 230 is then secured to the base of the toe. The second armor cone end opening 250 is provided at a tip of the second armor cone end 220 allowing for inspection of the toenail and application of medicine to speed recovery and prevent infection.

It is to be understood that the correction protection tool for an ingrown toenail is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A correction protection tool for an ingrown toenail, the tool comprising:
   an armor stocking having a first armor stocking end and a second armor stocking end;
   the first armor stocking end having a first armor stocking end opening adapted to receive a toe;
   the second armor stocking end having a second armor stocking end opening adapted to expose said ingrown toenail of the toe;
   an armor cone having a first armor cone end and a second armor cone end;
   the first armor cone end having a first armor cone end opening adapted to receive the armor stocking; and
   the second armor cone end surrounding the second armor stocking end;
   wherein the armor cone is adapted to protect said ingrown toenail;
   wherein the second armor cone end comprises a second armor cone end opening at a tip of the second armor cone end; and
   wherein the second armor cone end opening is adapted to allow for inspection of said ingrown toenail.

2. The tool as recited in claim 1, wherein the second armor stocking end opening is adapted to fit around said ingrown toenail.

3. The tool as recited in claim 1, wherein the first armor stocking end further comprises an armor stocking self-adhesive bandage adapted to fix the armor stocking to a base of the toe.

4. The tool as recited in claim 1, wherein the armor stocking is made of an elastic, soft, flexible silicone adapted to fit around the toe.

5. The tool as recited in claim 1, wherein the first armor cone end comprises an armor cone self-adhesive bandage.

6. The tool as recited in claim 1 wherein the armor cone is a hard silicone cover.

7. A correction protection tool for an ingrown toenail, the tool comprising:
   an armor stocking having a first armor stocking end and a second armor stocking end;
   the first armor stocking end having a first armor stocking end opening adapted to receive said ingrown toenail and an armor stocking self-adhesive bandage adapted to adhere the armor stocking to a base of the toe;
   the second armor stocking end having a second armor stocking end opening adapted to expose said ingrown toenail of the toe, the second armor stocking end opening adapted to fit around the toenail;
   an armor cone having a first armor cone end and a second armor cone end;
   the first armor cone end having a first armor cone end opening adapted to receive the armor stocking and an armor cone self-adhesive bandage; and
   the second armor cone end surrounding the second armor stocking end; an opening at a tip of the second armor cone end adapted to allow for inspection of said ingrown toenail;
   wherein the armor cone is adapted to protect the ingrown toenail.

8. The tool as recited in claim 7, wherein the armor cone is a hard silicone cover.

9. The tool as recited in claim 7, wherein the armor stocking is made of an elastic, soft, flexible silicone adapted to fit around the toe.

* * * * *